United States Patent
Chan et al.

(10) Patent No.: US 10,315,007 B2
(45) Date of Patent: Jun. 11, 2019

(54) VASCULAR ACCESS SYSTEM AND METHOD OF USE

(71) Applicants: STRYKER CORPORATION, Kalamazoo, MI (US); STRYKER EUROPEAN HOLDINGS I, LLC, Kalamazoo, MI (US)

(72) Inventors: Jason Chan, Union City, CA (US); Huey Chan, San Jose, CA (US)

(73) Assignees: Stryker Corporation, Kalamazoo, MI (US); Stryker European Holdings I, LLC, Kalamazoo, MI (US)

( * ) Notice: Subject to any disclaimer, the term of this patent is extended or adjusted under 35 U.S.C. 154(b) by 708 days.

(21) Appl. No.: 14/798,901

(22) Filed: Jul. 14, 2015

(65) Prior Publication Data

US 2016/0015935 A1    Jan. 21, 2016

Related U.S. Application Data (60) Provisional application No. 62/024,707, filed on Jul. 15, 2014.

(51) Int. Cl.
| | |
|---|---|
| *A61M 25/01* | (2006.01) |
| *A61M 25/04* | (2006.01) |
| *A61M 25/09* | (2006.01) |

(52) U.S. Cl.
CPC ........ *A61M 25/0105* (2013.01); *A61M 25/09* (2013.01); *A61M 25/04* (2013.01);
(Continued)

(58) Field of Classification Search
CPC ................ A61M 25/0105; A61M 2025/09125
See application file for complete search history.

(56) References Cited

U.S. PATENT DOCUMENTS

| | | | | |
|---|---|---|---|---|
| 4,728,319 | A | * | 3/1988 | Masch ........... A61B 17/320758 600/585 |
| 4,926,858 | A | * | 5/1990 | Gifford, III ...... A61B 17/22031 604/22 |

(Continued)

FOREIGN PATENT DOCUMENTS

| | | |
|---|---|---|
| WO | 2007/022592 | 3/2007 |
| WO | 2007133736 A2 | 3/2007 |

(Continued)

OTHER PUBLICATIONS

International Search Report and Written Opinion for International Application No. PCT/US2015/040332. Applicant Stryker Corporation, dated Nov. 2, 2015 (11 pages).

*Primary Examiner* — Bhisma Mehta
*Assistant Examiner* — Matthew A Engel
(74) *Attorney, Agent, or Firm* — Vista IP Law Group LLP (57) ABSTRACT

A vascular access system includes a catheter having an inner lumen in communication with an open distal end; a guidewire at least partially positioned in the catheter lumen and extending out the open distal end thereof, respective proximal and distal stops secured to the guidewire; and a centering device slidably mounted on the guidewire such that the centering device may freely within the catheter lumen relative to the guidewire between the proximal and distal stops, wherein the centering device substantially aligns a longitudinal axis of the catheter with a longitudinal axis of the guidewire proximate the centering device.

12 Claims, 10 Drawing Sheets

(52) U.S. Cl.
CPC ............... *A61M 2025/0183* (2013.01); *A61M 2025/09008* (2013.01); *A61M 2025/09183* (2013.01)

(56) References Cited

U.S. PATENT DOCUMENTS

| | | | |
|---|---|---|---|
| 5,938,582 A | 8/1999 | Ciamacco et al. | |
| 5,989,210 A * | 11/1999 | Morris | A61B 17/32037 604/22 |
| 6,068,611 A | 5/2000 | Loffler et al. | |
| 6,290,720 B1 * | 9/2001 | Khosravi | A61F 2/07 623/1.13 |
| 6,371,971 B1 * | 4/2002 | Tsugita | A61F 2/01 606/200 |
| 6,454,775 B1 * | 9/2002 | Demarais | A61B 17/320725 606/128 |
| 6,579,302 B2 | 6/2003 | Duerig et al. | |
| 6,802,835 B2 | 10/2004 | Rabiner et al. | |
| 6,887,256 B2 * | 5/2005 | Gilson | A61F 2/0095 606/200 |
| 6,945,989 B1 * | 9/2005 | Betelia | A61F 2/95 623/1.11 |
| 7,101,380 B2 * | 9/2006 | Khachin | A61B 17/221 606/127 |
| 7,547,304 B2 | 6/2009 | Johnson | |
| 7,951,243 B2 * | 5/2011 | Boyle, Jr. | A61B 19/34 134/166 C |
| 8,491,614 B2 | 7/2013 | LeMaitre et al. | |
| 8,597,454 B2 | 12/2013 | Parker et al. | |
| 8,900,265 B1 * | 12/2014 | Ulm, III | A61B 17/221 606/159 |
| 9,034,007 B2 * | 5/2015 | Janardhan | A61F 2/013 600/434 |
| 2004/0230219 A1 | 11/2004 | Roucher | |
| 2009/0082800 A1 * | 3/2009 | Janardhan | A61F 2/013 606/200 |
| 2009/0247988 A1 | 10/2009 | Johnson | |
| 2011/0125181 A1 * | 5/2011 | Brady | A61B 17/22031 606/200 |
| 2013/0144326 A1 * | 6/2013 | Brady | A61F 2/01 606/200 |
| 2014/0180387 A1 * | 6/2014 | Khenansho | A61F 2/966 623/1.12 |

FOREIGN PATENT DOCUMENTS

| | | |
|---|---|---|
| WO | 2011133736 A2 | 10/2011 |
| WO | WO 2014/066412 A1 | 5/2014 |

* cited by examiner

VASCULAR ACCESS SYSTEM AND METHOD OF USE

RELATED APPLICATION DATA

The present application claims the benefit under 35 U.S.C. § 119 to U.S. provisional patent application Ser. No. 62/024,707, filed Jul. 15, 2014. The foregoing application is hereby incorporated by reference in its entirety.

FIELD OF INVENTION

The present disclosure pertains generally to systems and methods for accessing a vascular system. More particularly, the present disclosure pertains to systems and methods for facilitating the navigation of elongate medical devices through the vasculature to a target site in a blood vessel.

BACKGROUND

The use of intravascular medical devices has become an effective method for treating many types of vascular disease. In general, a suitable intravascular device, such as an intravascular catheter, is inserted into a patient's vascular system, and then navigated through the patient's vasculature to a target site to be treated. Using this method, virtually any target site in the patient's vascular system may be accessed, including the coronary, cerebral, and peripheral vasculature.

Catheters are often utilized for intraluminal procedures, including delivery of medical implants or embolic materials, at a desired location within a body lumen. A catheter typically enters the patient's vasculature at a convenient location, such as a blood vessel in the neck or near the groin. Once a distal portion of the catheter has entered the patient's vascular system, the distal tip may be urged toward the target site by applying an axial force to the proximal portion of the catheter. Catheters having a relatively high level of pushability and kink resistance more effectively communicate this axial force to be "steered" into the target site. Such treatment catheters may need to be navigated a tortuous path through the patient's vasculature, including travel within relatively fragile blood vessels, such as in the brain, and are often required to change direction and to even double back on themselves. Thus, the treatment catheters must be flexible enough to navigate tortuous path, while avoiding damaging the blood vessels through which they travel, in addition to having a relatively high level of torqueability to facilitate the steering process.

It is well-known to employ a guidewire to facilitate the navigation of catheters through the vascular system. Such guidewires include so-called "over-the-wire" and "rapid-exchange" systems. In an "over-the-wire" system, a catheter is introduced into the patient over a guidewire that has been previously introduced into the vasculature; the guidewire extends through the entire length of the catheter, i.e., through an axial lumen of the catheter. In a "rapid-exchange" system, the guidewire extends through only a distal portion of the catheter from the distal tip to a guidewire port located proximal of the distal tip.

A catheter being pushed through a patient's vasculature (whether or not assisted by a guidewire) will usually follow a path of least resistance through a blood vessel, and may end up inadvertently colliding into and/or scraping the inner wall of the vessel being navigated, especially in a tortuous vascular system, and at bifurcated vessels walls, aneurysms, and other anatomical features. Such navigational difficulties can undesirably increase the time needed for positioning the distal end of the catheter at the target location for performing a medical procedure, as well as further increase the risk of trauma or damage to the blood vessels as the catheter is navigated there through.

Figures 1A, 1B:
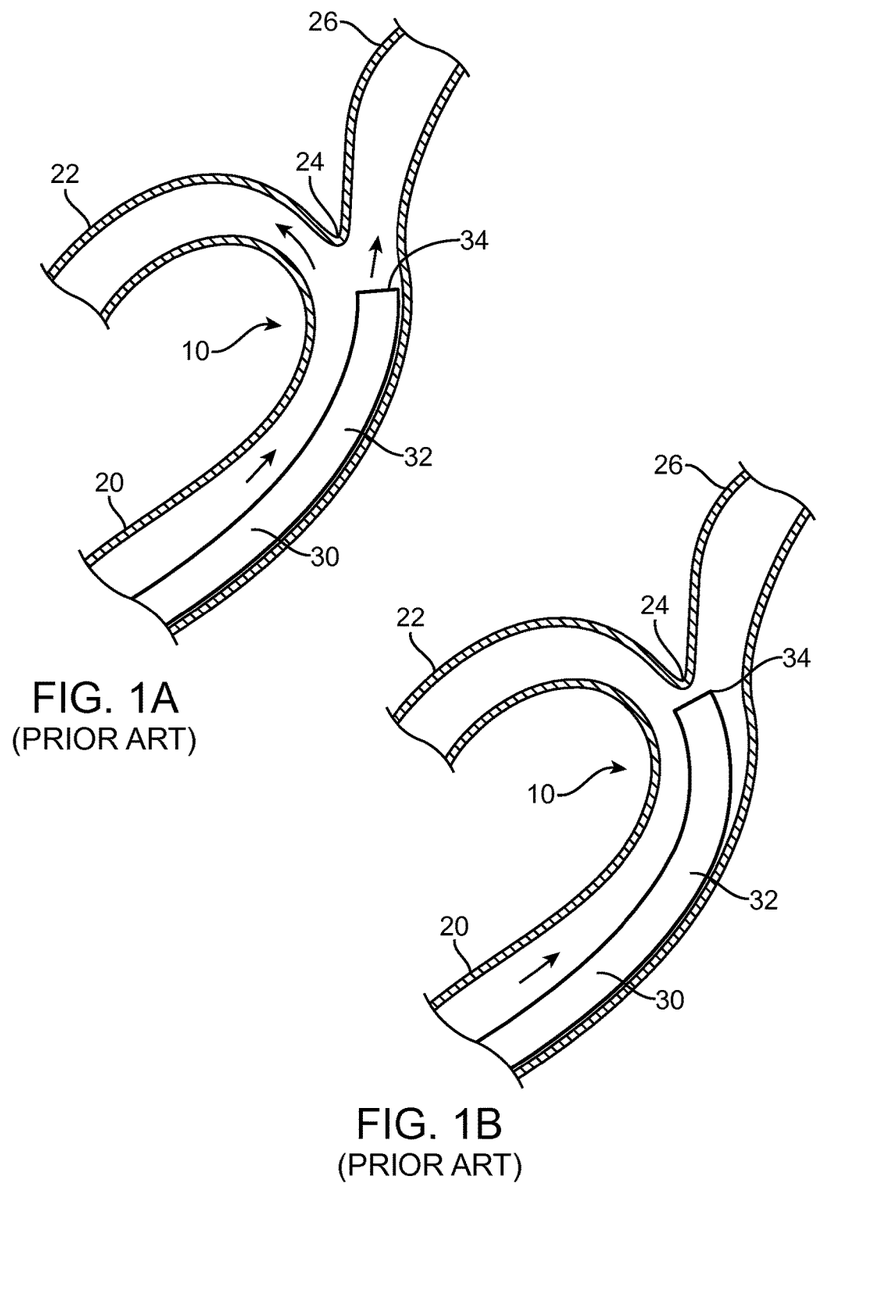
FIGS. 1A-B are cross-sectional views of a conventional (Prior Art) catheter distal end portion being introduced into a bifurcated vasculature.

By way of illustration, FIGS. 1A-B illustrate a method of accessing a bifurcated vasculature 10 using a conventional catheter 30, without guidewire assistance. The bifurcated vasculature 10 includes a main blood vessel 20, a first blood vessel branch 22, a second blood vessel branch 26, and a bifurcated angle 24 between the first 22 and second 26 branches. The catheter 30 distal portion 32 is advanced through the main blood vessel 20 and maneuvered to access a target site within the first blood vessel branch 22. Usually, the catheter 30 advances along a path of least resistance by sliding through the main blood vessel 20, and favoring access to the second blood vessel branch 26 (FIG. 1A). While corrective action may be taken by the attending physician to maneuver the catheter distal portion 32 into the desired second blood vessel branch 26, a distal tip 34 of the catheter 30 may still catch and bump the bifurcated angle 24 (FIG. 1B), which can damage the blood vessel, particularly, a relatively fragile vessel, if in the brain, increasing risk of an undesirable rupture or piercing of the blood vessel walls.

Figures 2A, 2B, 2C:
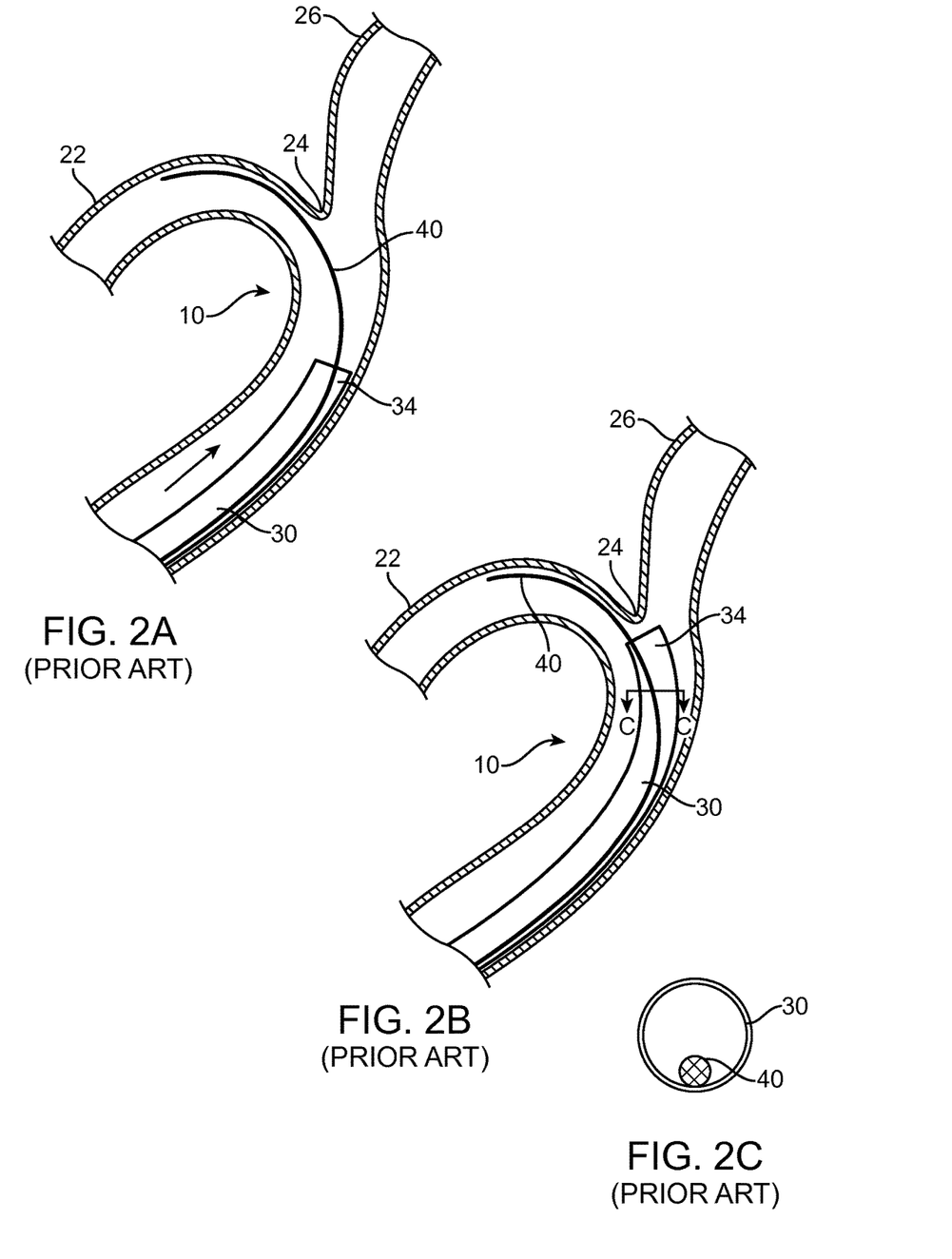
FIGS. 2A-C are cross-sectional views of a conventional (Prior Art) catheter and guidewire system being introduced into a bifurcated vasculature.

By way of further illustration, FIGS. 2A-C illustrate a method of accessing the bifurcated vasculature 10, in which a guidewire 40 is used to facilitate navigation of the catheter 30. With the guidewire 40 is introduced into the desired first blood vessel branch 22 and the catheter 30 is advanced over the guidewire 40 (FIG. 2A), the catheter distal tip 34 may still catch and cause trauma to the bifurcated angle 24 (FIG. 2B); since the guidewire 40 is not disposed in a concentric configuration within (i.e., is not axially aligned with) the catheter 30. As shown in FIG. 2C the guidewire 40 off-center from the catheter 30, which may force a withdrawal of the catheter 30, with further attempts to advance the catheter distal end tip 34 into the desired first blood vessel branch 22 increasing the risk of trauma to the blood vessel.

Accordingly, it would be desirable to provide a vascular access system for navigating a catheter to a target site in a vasculature in a manner wherein the catheter tends to stay centered within the lumen of a vessel being navigated, thereby minimizing undesired contact with vessel walls and other navigational difficulties caused by misalignment of the catheter.

SUMMARY

In one embodiment of the disclosed inventions, a vascular access system includes a catheter having an inner lumen in communication with an open distal end of the catheter; an elongate, flexible navigational member at least partially positioned in the catheter lumen, with a distal end portion of the navigational member extending out the open distal end of the catheter, the navigational member and catheter being movable relative to each other; a proximal stop secured to the navigational member at a first location; a distal stop secured to the navigational member at a second location distal of the first location; and a centering device slidably mounted on the navigational member between the proximal and distal stops so that the centering device may move freely within the catheter lumen relative to the navigational member between the proximal and distal stops, wherein the centering device substantially aligns a longitudinal axis of the catheter with a longitudinal axis of the navigational member proximate the centering device.

In various embodiments, the centering device is positioned within the catheter lumen. In one such embodiment with the centering device positioned within the catheter lumen, the open distal end of the catheter being tapered or otherwise shaped so as to allow travel of the distal stop, but prevent travel of the centering device, respectively, there through.

In various embodiments, the centering device has a proximal portion, distal portion and central lumen through which the navigational member extends, wherein the proximal portion has a cross-section larger than a cross-section of the distal portion. In one such embodiment, the respective proximal and distal portions have arcuate, atraumatic shapes.

In various embodiments, the centering device has a proximal portion, middle portion, distal portion and central lumen through which the navigational member extends, wherein the middle portion has a cross-section that is larger than respective cross-sections of the proximal and distal portions. In one such embodiment, the respective proximal and distal portions have arcuate, atraumatic shapes.

In various embodiments, the centering device may be made of a biocompatible polymer, such as silicone, and has an olive-like, football-like, prolate spheroid, ellipsoid, conical and/or elongate configuration.

In various embodiments, the proximal and distal stops are made from a metal, metal alloy, polymer and/or metal-polymer composite, and are secured to the navigational member by an adhesive or thermal bonding.

In various embodiments, the navigational member may be a conventional guidewire.

Other and further aspects and features of embodiments of the disclosed inventions will become apparent from the ensuing detailed description in view of the accompanying figures.

DETAILED DESCRIPTION

For the following defined terms, these definitions shall apply, unless a different definition is set forth in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5). As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

Figure 3A:
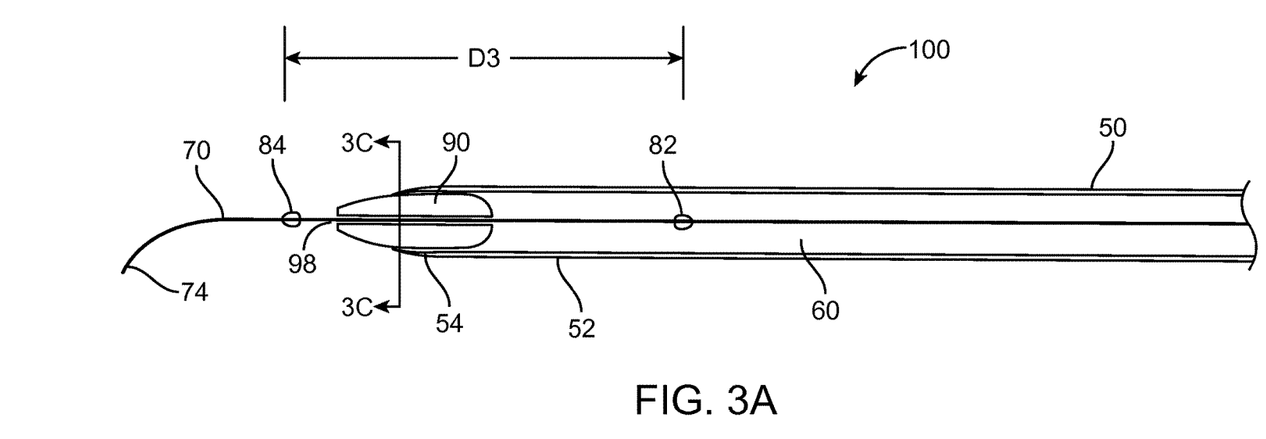
FIGS. 3A-C are cross sectional views of vascular access systems according to embodiments of the disclosed inventions.

FIG. 3A illustrates a vascular access system 100, constructed in accordance with one embodiment of the disclosed inventions. The vascular access system 100 includes an outer elongate member 50 (i.e. catheter) having a proximal end portion (not shown), a distal end portion 52, and a lumen 60 extending therebetween. The catheter 50 further includes an open distal end 54 having a tapered configuration with an inner diameter less than the inner diameter of catheter lumen in the distal end portion 52 of the catheter. The catheter 50 may include one or more, or a plurality of regions along its length having different configurations and/or characteristics, and may be formed of suitable materials, such as, polymeric materials, metals, alloys or the like, or combinations thereof. For example, the distal portion 52 of the catheter 50 may have an outer diameter less than the outer diameter of the proximal portion (not shown) to reduce the profile of the distal portion 52 and help facilitate navigation in tortuous portion of the vasculature.

Furthermore, the distal portion 52 may be more flexible than the proximal portion. Generally, the proximal portion may be formed from material that is stiffer than the distal portion 52, so that the proximal portion has sufficient pushability to advance through the patient's vascular system, while the distal portion 52 may be formed of a more flexible material so that the distal portion 52 may remain flexible and track more easily, for example, over a guidewire to access remote locations in tortuous regions of the vasculature. In some instances, the proximal and/or distal portions may include a reinforcement layer, such a braided layer or coiled layer to enhance the pushability and kink resistance of the catheter 50. In some cases, the distal end tip 54 may include a radiopaque material or marker to aid in visualization.

The vascular access system 100 further includes an inner elongate member 70, which may be a conventional guidewire modified as described herein, slidably disposed in the catheter lumen 60. The elongate member 70, hereinafter referred to as a guidewire, is preferably made of a torqueable material; some examples can include metals, metal alloys, polymers, metal-polymer composites, and the like, or any other suitable material. For example, the guidewire 70 may include nickel-titanium alloy, stainless steel, a composite of nickel-titanium alloy and stainless steel. In some cases, guidewire 70 can be made of the same material along its length, or in some embodiments, can include portions or sections made of different materials. In some embodiments, the material used to construct guidewire 70 is chosen to impart varying flexibility and stiffness characteristics to different portions of guidewire 70. For example, the proximal region can be formed of stainless steel, and the distal region can be formed of a nickel-titanium alloy. However, any suitable material or combination of material may be used for the guidewire 70, as desired. The guidewire 70 may have shapeable or pre-shaped distal tip 74, preferably including an atraumatic distal end, to aid in the advancement of the guidewire 70. In some cases, the distal tip 74 may include a radiopaque material or marker to aid in visualization.

In accordance with embodiments of the disclosed inventions, the guidewire 70 is provided respective proximal and distal stops, 82 84, secured to a distal portion thereof. The proximal and distal stops 82 and 84 may be made of metals, metal alloys, polymers, metal-polymer composites, and the like, or any other suitable materials, that are fixedly secured to the guidewire 70 by adhesive, thermal bonding or the like, or combinations thereof, or by any other suitable method. The stops 82 and 84 may be radiopaque, in which case they also function as markers, and may have a spherical, conical, elongate or any other suitable configuration, so long as the stops 82 and 84 function to adequately retain a centering device 90 slidably mounted on the guidewire 70 between the stops 82 and 84, as described below.

Figure 4A:
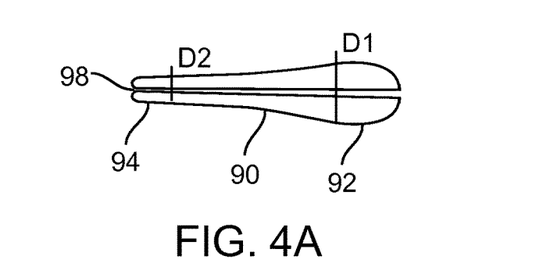
FIGS. 4A-C are cross sectional views of centering devices according to embodiments of the disclosed inventions.
Figure 4B:
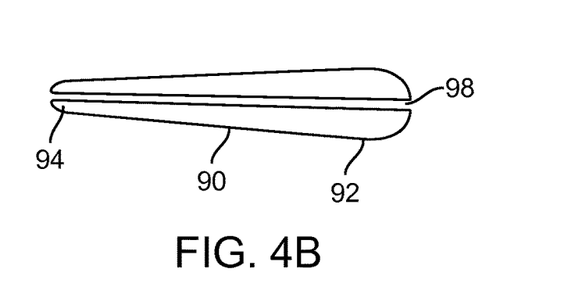

In particular, the illustrated centering device 90 of FIGS. 3A, 4A-B, and 5A-6C has a "pitted olive" configuration, with a central lumen 98 passing there through. It should be appreciated that the centering device 90 may have an alternate shape, such as bullet, conical, or other suitable configuration in which a diameter D1 of a proximal portion 92 of the centering device 90 is greater that a D2 of a distal portion 94 of the centering device 90 (best seen in FIG. 4A). A suitable centering device 90 includes non-traumatic proximal and distal portions, 92 and 94, respectively, having substantially rounded shoulders-like configurations with gentle slopes there between or having further elongated configurations, as shown in FIGS. 4A-B, while avoiding configurations that create angular shapes. The centering device 90 may be made of low durometer materials, such as polyurethane, pebax, silicone or the like, or combination thereof. Alternatively, the centering device 90 may be made of metals, metal alloys, or metal-polymer materials with suitable biocompatible properties. Additionally, the centering device 90 may include a radiopaque material, marker members or marker bands made of radiopacified polymers or other suitable radiopaque material to aid in visualization. The centering device 90 may include a lubricious coating to facilitate advancement and withdrawal of the device 90 within the catheter 50.

The centering device 90 is slidably disposed over the guidewire 70 between the respective proximal and distal stops 82 and 84, such that the stops 82 and 84 limit movement of the centering device 90 to the distance D3 between the stops 82 and 84, and allow for placement and/or withdrawal of the centering device 90 at the distal end tip 54 of catheter 50, as further described below in conjunction with FIGS. 5A-B. The tapered open distal end 54 of the catheter 50 also prevents and/or limits movement of the centering device 90 out of a distal end opening 56 of the catheter 50, so that the distal end tip 54 snuggling held, at least, the proximal portion 92 of the centering device 90 (FIG. 3A). When the centering device 90 is disposed at the distal end tip 54 of the catheter 50, the centering device 90 is configured to place the guidewire 70 in a concentric configuration relative to the catheter 50 distal end portion 52 (FIG. 3C).

Figure 3B:
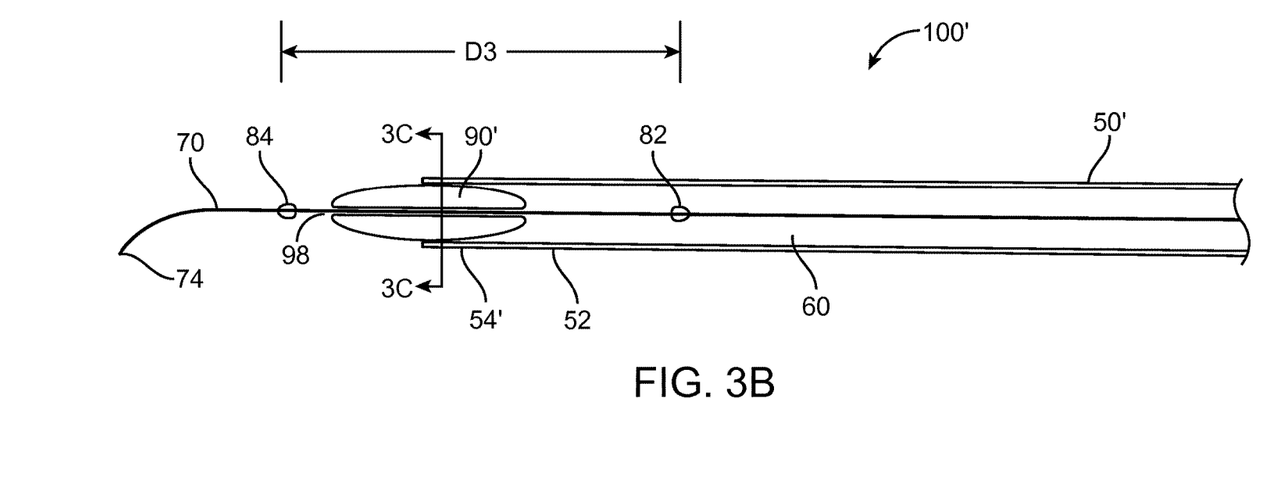

FIG. 3B illustrates an alternative embodiment of the vascular access system 100' constructed in accordance with the disclosed inventions. For ease in illustration, the features, functions, and configurations of the vascular access system 100' that are the same as in system 100 of FIG. 3A are given the same reference numerals. The vascular access system 100' of FIG. 3B, includes a catheter 50' having a proximal end portion (not shown), a distal end portion 52, and a lumen 60 extending therebetween. The catheter 50' further includes an open distal end 54' having an inner diameter that is substantially the same as the inner diameter of the distal end portion 52 of the catheter, i.e. a non-tapered distal end 54'.

Figure 4C:
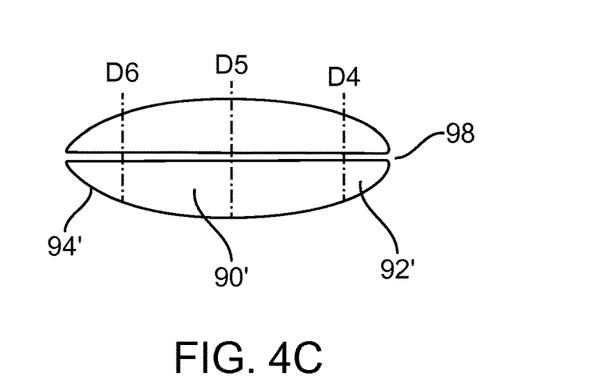

The vascular access system 100' further includes a centering device 90' slidably mounted on the guidewire 70 between the stops 82 and 84. The centering device 90' of FIGS. 3B, 4C, and 7A-E, have an American football-like configuration, with a central lumen 98 passing there through. It should be appreciated that the centering device 90' may have a prolate spheroid, ellipsoid, or other suitable configuration in which diameters D4 and D6 are substantially the same, and diameter D5 is larger than D4 or D6 (best seen in FIG. 4C). The centering device 90' is slidably disposed over the guidewire 70 between the respective proximal and distal stops 82 and 84, such that the stops 82 and 84 limit movement of the centering device 90' to the distance D3 between the stops 82 and 84, and allow for advancement and/or withdrawal of the centering device 90' through a vasculature of a patient and/or lumen 60 of catheter 50', as further described below in conjunction with FIGS. 7A-E.

Figure 3C:
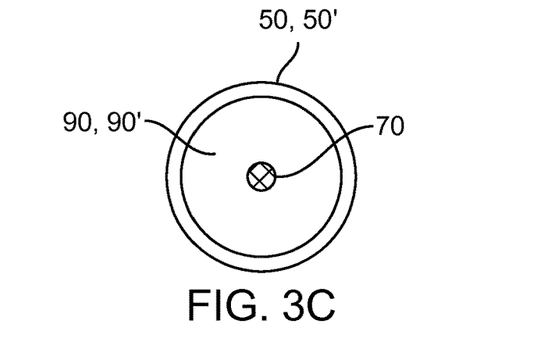

When the centering device 90' is disposed at the distal end tip 54' of the catheter 50', the centering device 90' is configured to place the guidewire 70 in a concentric configuration relative to the catheter 50' distal end portion 52 (FIG. 3C). It will be appreciated that the non-tapered open distal end 54' of the catheter 50' allows movement of the centering device 90' out of the distal end opening 56 the catheter 50' (FIG. 5C).

Referring back to FIGS. 5A-B, these embodiments illustrate an exemplary method of accessing a blood vessel 150 and navigating within a blood vessel lumen 155 using the vascular access system 100, constructed in accordance with the disclosed inventions. FIG. 5A illustrates the introduction of the guidewire 70 within the catheter 50 and advancement of the centering device 90 towards the distal end tip 54 and distal end opening 56. When the guidewire 70 is advanced through the lumen 60 of the catheter, the proximal stop 82 engages the proximal end portion 92 pushing and moving the centering device 90 towards the distal end tip 54 of the catheter 50, until the centering device 90 is engaged and snuggling held by the distal end tip 54 (FIG. 3A). FIG. 5B illustrates the withdrawal of the guidewire 70 from the catheter 50 and consequent withdrawal of the centering device 90. When the guidewire 70 is withdrawn through the lumen 60 of the catheter, the distal stop 84 engages the distal end portion 94 pushing and moving the centering device 90 towards the proximal portion of the catheter 50, until the centering device 90 is disengaged by the distal end tip 54. The guidewire 70 including the centering device 90 may be withdrawn from the catheter after a desired target site is reached by the distal end tip 54 of the catheter.

Figure 5A:
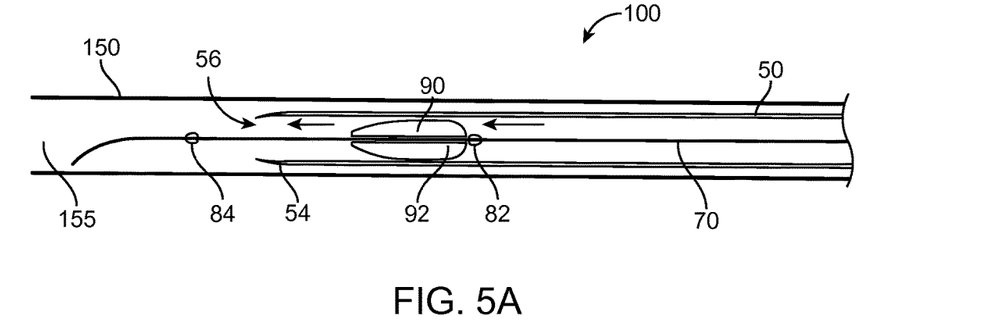
FIGS. 5A-C are cross-sectional views of a method of accessing a vasculature system using the vascular access systems of FIGS. 3A-B.
Figure 5B:
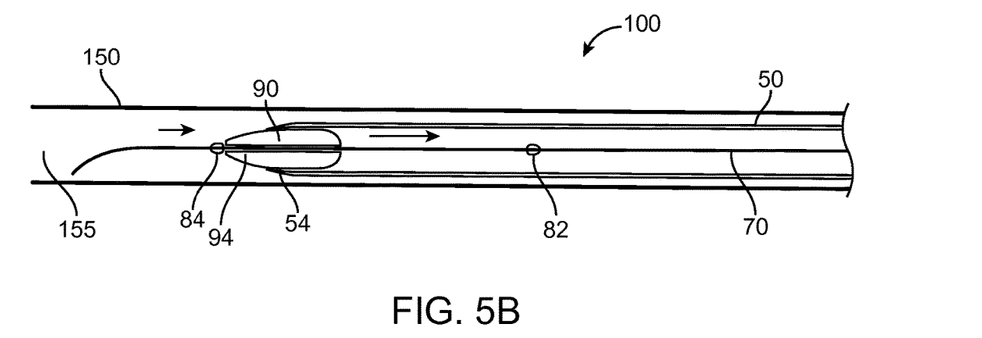
Figure 5C:
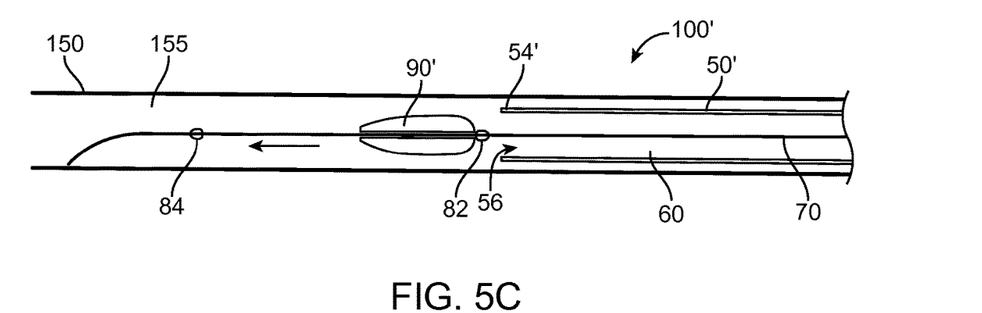

It should be appreciated that the centering device 90' of vascular access system 100' is advanced and/or withdrawn within the lumen 60 of the catheter 50' using the guidewire 70 and stops 82 and 84 interface, similar to the above description of FIGS. 5A-B. However, the centering device 90' may be advanced out of the distal end opening 54' the catheter 50', as shown in FIG. 5C, since the distal end tip 54' of catheter 50' is non-tapered and therefore allows advancement of the centering device 90' out of the open distal end 54' of the catheter 50'.

Figures 6A, 6B:
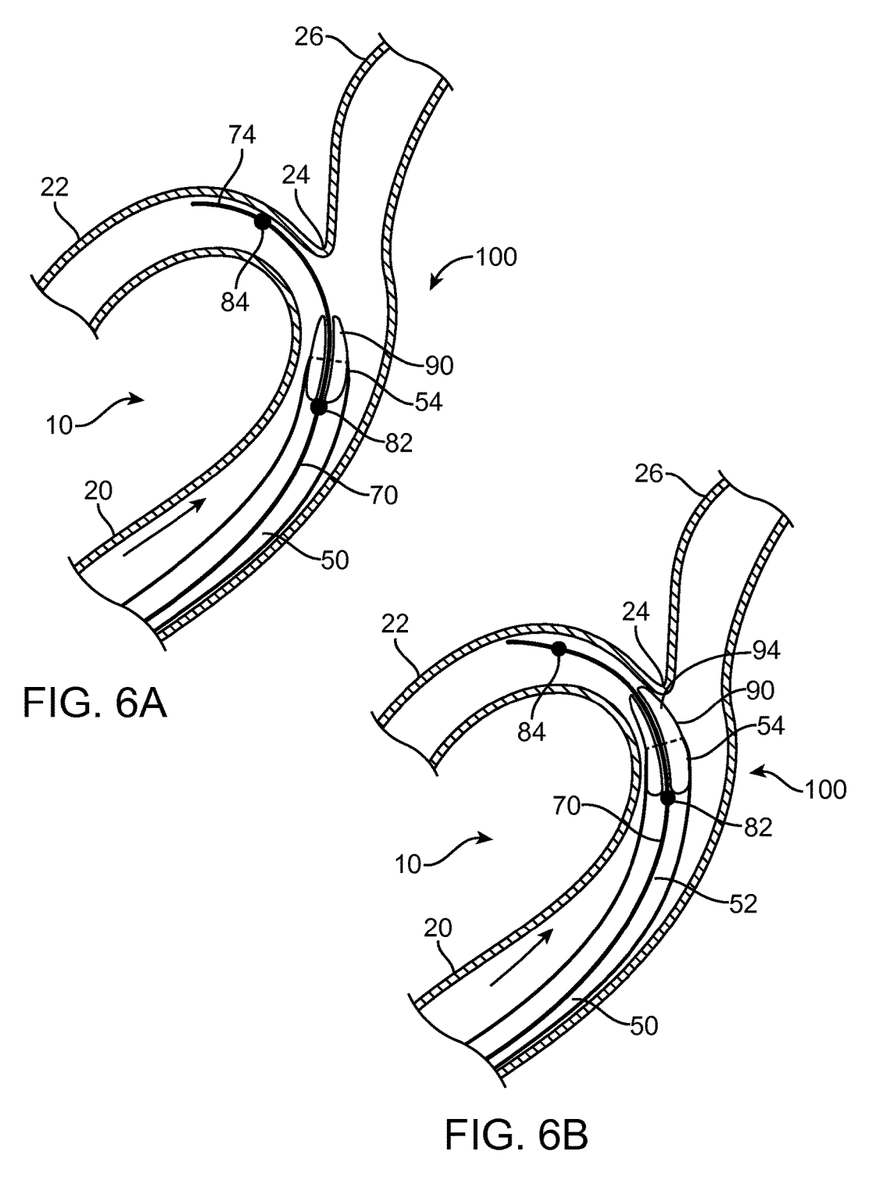
FIGS. 6A-C are cross-sectional views of a method of accessing a bifurcation in a vasculature system using the vascular access system of FIG. 3A.
Figure 6C:
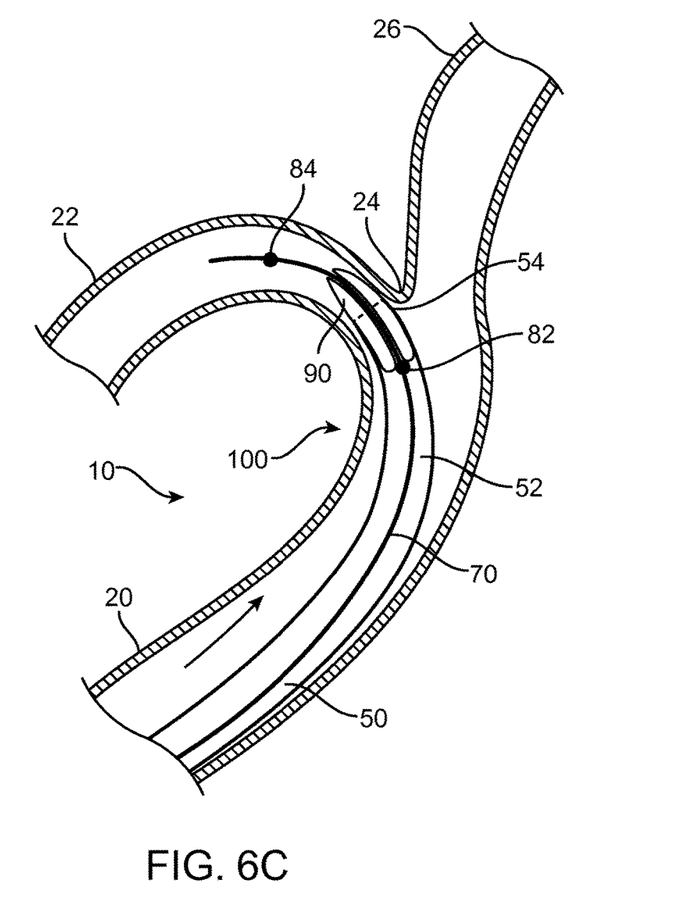

FIGS. 6A-C illustrate an exemplary method of accessing the bifurcated blood vessel 10 using the vascular access system 100, constructed in accordance with embodiments of the disclosed inventions. After gaining access to the vasculature region of a patient, the vascular access system 100 having the guidewire 70 loaded therein and having the centering device 90 disposed within the distal end tip 54 of the catheter 50, is inserted into main blood vessel 20 (FIG. 6A). The access system 100 is advanced until the distal tip 74 of the guidewire 70 is inserted into the desired first blood vessel branch 22, such that the distal portion 52 of the catheter 50 is disposed toward a target site within the first blood vessel branch 22. The access system 100 is then further advanced so that the distal portion 94 of the centering device 90 is positioned at an entrance portion 23 first blood vessel branch 22, which allows for advancement of the system catheter 50 in a substantially smooth and non-traumatic fashion, while avoiding catching and bumping against the bifurcated angle 24 of the blood vessel (FIGS. 6B-C). The centering device 90 allows the distal end tip 54 and distal portion 52 of the catheter 50 to be centered and concentric with respect to the blood vessel branch 22, and further centers the guidewire 70 within the lumen 60 of the catheter 50.

After the distal end tip 54 of the catheter 50 has reached the target site, the guidewire 70 including the centering device 90 may be withdrawn (FIG. 5B), so that the lumen 60 of the catheter 50 is substantially free and available for a desired intravascular application (e.g. delivery of medical implants, or embolic materials) (not shown). After completion of the desired intravascular application, the catheter 50 is withdrawn from the bifurcated blood vessel 10 and vasculature of a patient.

It will be appreciated that, after the centering device 90 is engaged and snuggling held by distal end tip 54 of the catheter 50 (FIG. 3A), the catheter 50, the centering device 90, and the guidewire 70, are jointly advanced through the vasculature into the target site in a blood vessel, when using the vascular access system 100 as illustrated in FIGS. 6A-C. In contrast, the catheter 50' of the vascular access system 100' moves relative to the guidewire 70 and centering device 90' during advancement into the target site in a blood vessel (FIGS. 7A-E), as described below.

Figures 7A, 7B:
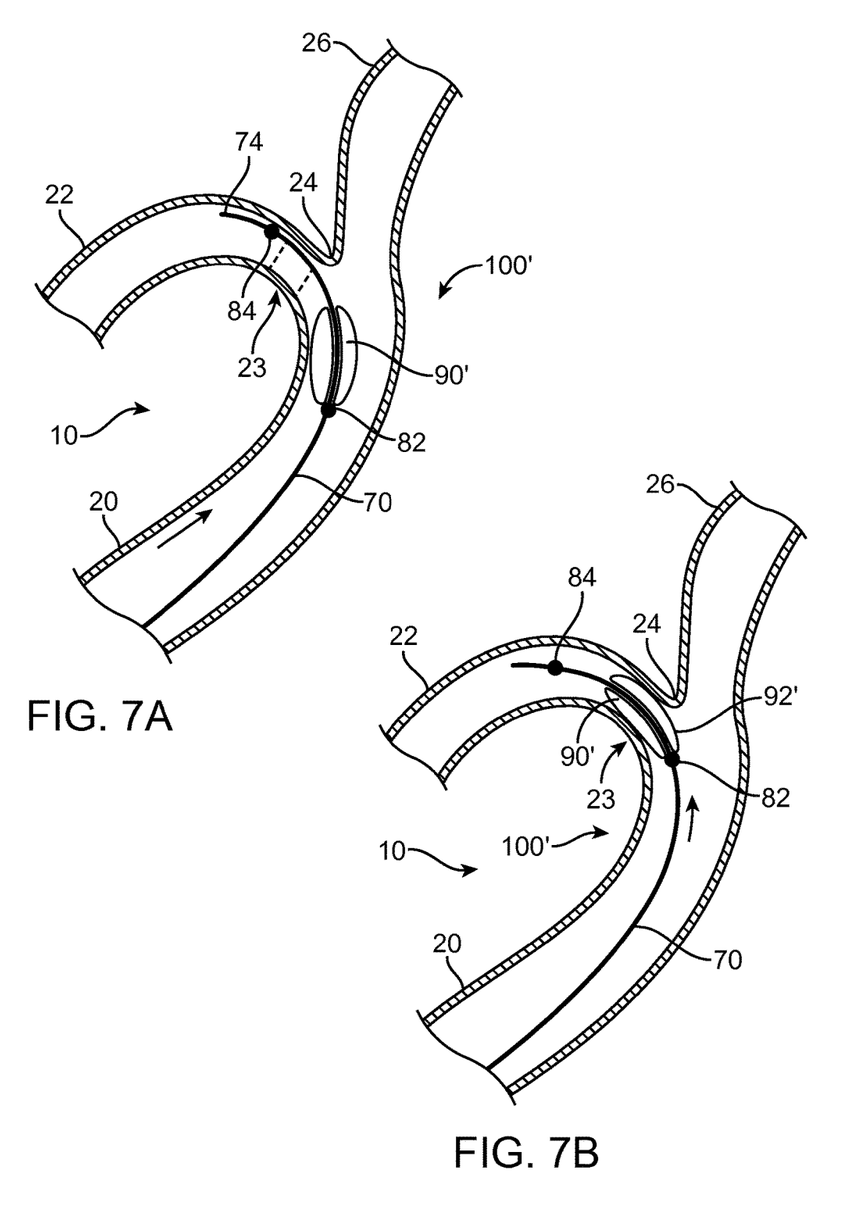
FIGS. 7A-E are cross-sectional views depicting a method of accessing a bifurcation in a vasculature system using the vascular access system of FIG. 3B.

FIGS. 7A-E illustrate an exemplary method of accessing the bifurcated blood vessel 10 using the vascular access system 100', constructed in accordance with embodiments of the disclosed inventions. After gaining access to the vasculature region of a patient, the guidewire 70 carrying the centering device 90' is inserted into the main blood vessel 20, and is advanced into the desired first blood vessel branch 22. As the guidewire 70 is advanced, the proximal stop 82 engages the proximal end portion 92' pushing and moving the centering device 90' towards the entrance portion 23 of the first blood vessel branch 22 (FIG. 7A) until the centering device 90' is partially disposed at the entrance portion 23, so that the proximal portion 92' of the centering device 90' is disposed within the main blood vessel 20 and out of the entrance portion 23 of the first blood vessel branch 22 (FIG. 7B).

Figures 7C, 7D:
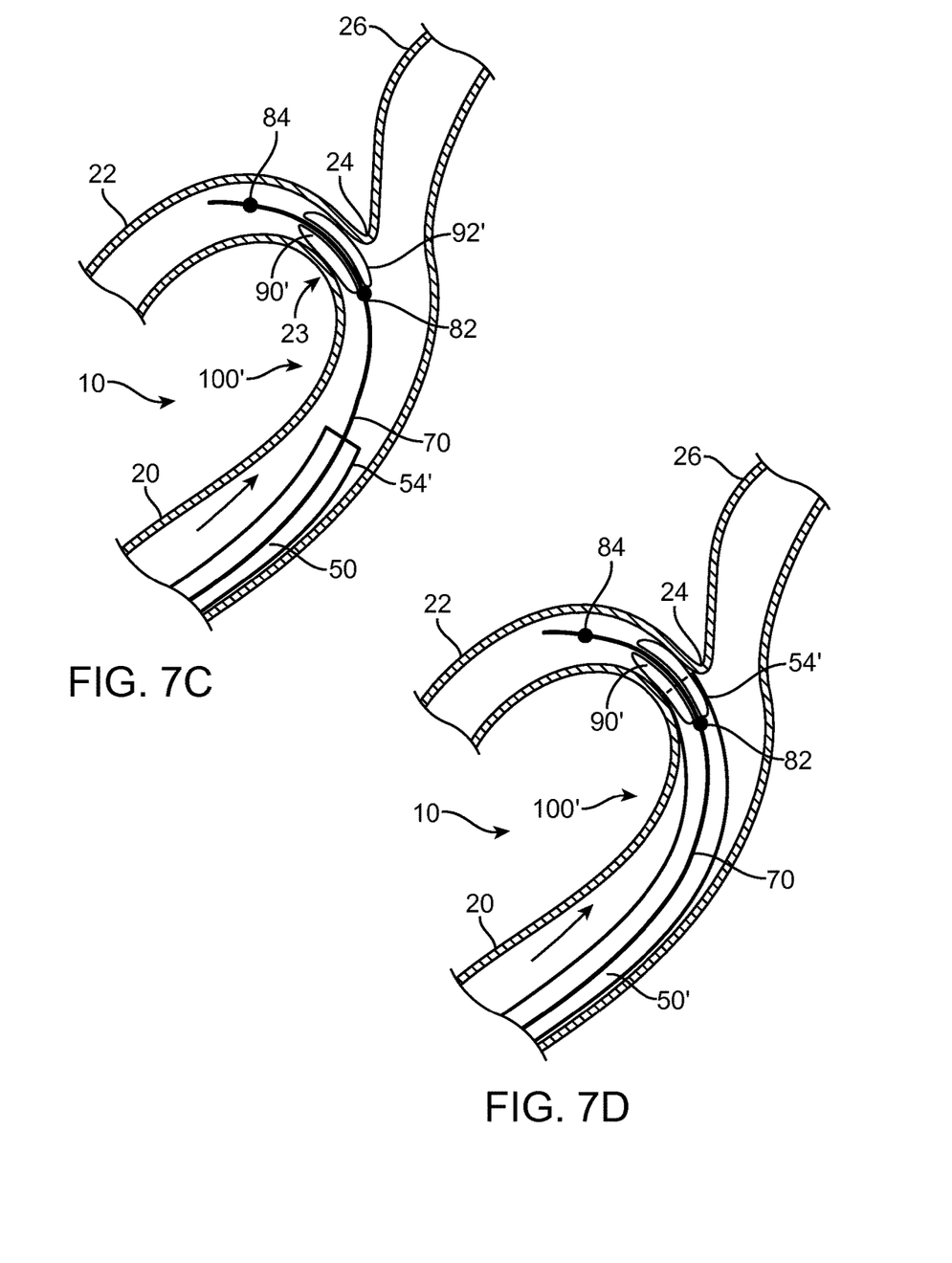

When the centering device 90' is partially disposed at the entrance portion 23 of the first blood vessel branch 22, having the proximal portion 92' "sticking out" of the entrance portion 23, the catheter 50' is advanced over the guidewire 70 (FIG. 7C) so that the distal tip end 54' reaches and "swallows" the proximal portion 92' of the centering device 90' (FIG. 7D). Having the centering device 90' disposed within the entrance portion 23 of the desired first blood vessel branch 22, allows for the guidewire 70 to be centered and concentric with respect to the blood vessel branch 22. Further, having the proximal portion 92' of the centering device 90' "sticking out" the entrance portion 23, allows the distal end tip 54' of the catheter 50' to advance over the centering device 90' substantially centered and concentric with respect to the blood vessel branch 22; allowing the catheter 50' to advance in a smooth and non-traumatic fashion, while avoiding catching and bumping against the bifurcated angle 24 of the blood vessel.

Figure 7E:
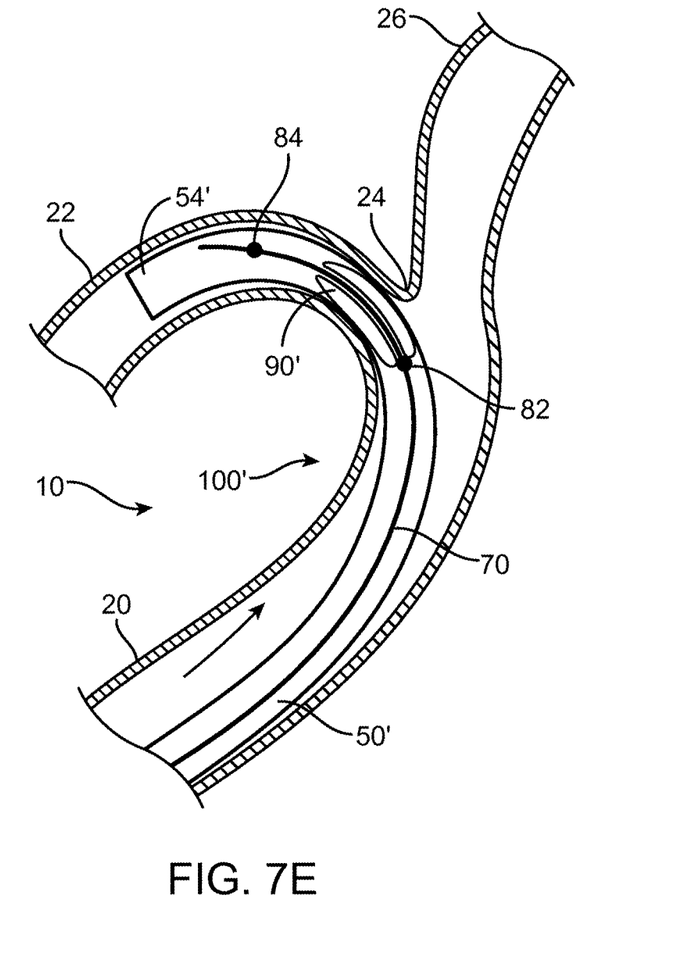

After gaining access to the entrance portion 23 of the desired first blood vessel branch 22, the catheter 50' may be further advanced into the blood vessel branch 22, swallowing the centering device 90' and moving beyond the location of the centering device 90' (FIG. 7E). Further, after the distal end tip 54' of the catheter 50' has reached the target site, the guidewire 70 including the centering device 90' may be withdrawn, so that the lumen 60 of the catheter 50' is substantially free and available for a desired intravascular application (e.g. delivery of medical implants, or embolic materials) (not shown). After completion of the desired intravascular application, the catheter 50' is withdrawn from the bifurcated blood vessel 10 and vasculature of a patient.

It will be appreciated that the exemplary methods illustrated in FIGS. 5A-C, 6A-C and 7A-E using the vascular access systems 100 and 100' may be contemplated to deliver tubular prosthesis, implants, stents, fluid diverters, agents or the like, in vascular and non-vascular applications.

Although particular embodiments have been shown and described herein, it will be understood that they are not intended to limit the disclosed inventions, and it will be apparent that various changes and modifications may be made (e.g., to the dimensions of various parts) without departing from the scope of the disclosed inventions, which are to be defined only by the claims and their equivalents. For instance, it will be appreciated that elements or components shown with any embodiment herein may be used on or in combination with other embodiments disclosed herein. The specification and drawings are, accordingly, to be regarded in an illustrative rather than restrictive sense.

What is claimed is:

1. A vascular access system, comprising:
   a catheter having an inner lumen in communication with an open distal end of the catheter;
   an elongate flexible navigational member at least partially positioned in the inner lumen, with a distal end portion of the navigational member extending out the open distal end of the catheter, the navigational member and catheter being movable relative to each other;
   a proximal stop secured to the navigational member at a first location;
   a distal stop secured to the navigational member at a second location distal of the first location; and
   a centering device having a proximal end and a distal end, the centering device slidably mounted on the navigational member between the proximal and distal stops so that the centering device may move freely longitudinally relative to the navigational member between the proximal and distal stops while being retained between the proximal and distal stops such that the proximal stop prevents the proximal end from moving proximally past the proximal stop and the distal stop prevents the distal end of the centering device from moving" to distinguish from " the open distal end of the catheter distally past the distal stop, wherein the centering device is positioned within the inner lumen of the catheter and substantially aligns a longitudinal axis of the catheter with a longitudinal axis of the navigational member proximate the centering device;

wherein the open distal end of the catheter is tapered or otherwise shaped so as to allow travel of the distal stop, but prevent travel of the centering device through the open distal end by direct contact between the centering device and the open distal end of the catheter.

2. A method of accessing a vasculature using the vascular access system of claim 1, comprising:

advancing the navigational member relative to the catheter until the centering device engages the open distal end of the catheter; and advancing the navigational member and catheter jointly through the vasculature after engagement of the centering device with the open distal end of the catheter.

3. The system of claim 1, the centering device having a proximal portion, distal portion and central lumen through which the navigational member extends, wherein the proximal portion has a cross-section larger than a cross-section of the distal portion.

4. The system of claim 3, wherein the respective proximal and distal portions have arcuate, atraumatic shapes.

5. The system of claim 1, the centering device comprising a proximal portion, middle portion, distal portion and central lumen through which the navigational member extends, wherein the middle portion has a cross-section that is larger than respective cross-sections of the proximal and distal portions.

6. The system of claim 5, wherein the respective proximal and distal portions have arcuate, atraumatic shapes.

7. The system of claim 1, wherein the centering device comprises an olive-like, football-like, prolate spheroid, ellipsoid, conical and/or elongate configuration.

8. The system of claim 1, wherein the centering device is made from a biocompatible polymer.

9. The system of claim 1, wherein the proximal and distal stops are made from a metal, metal alloy, polymer and/or metal-polymer composite.

10. The system of claim 1, wherein the proximal and distal stops are secured to the navigational member by an adhesive or thermal bonding.

11. The system of claim 1, wherein the navigational member comprises a guidewire.

12. A method of accessing a vasculature using the vascular access system of claim 1, comprising:

(a) advancing the navigational member relative to the open distal end of the catheter until the centering device is at least partially disposed at an entrance of a target blood vessel; and (b) advancing the catheter relative to the navigational member until the open distal end of the catheter encloses the centering device.

* * * * *

UNITED STATES PATENT AND TRADEMARK OFFICE
CERTIFICATE OF CORRECTION

PATENT NO. : 10,315,007 B2  
APPLICATION NO. : 14/798901  
DATED : June 11, 2019  
INVENTOR(S) : Jason Chan et al.

Page 1 of 1

It is certified that error appears in the above-identified patent and that said Letters Patent is hereby corrected as shown below:

In the Claims

At Column 9, Lines 8-10, Claim 1:
"the distal end of the centering device from moving" to distinguish from "the open distal end of the catheter distally past the distal stop,"

Should read:
-- the distal end of the centering device from moving distally past the distal stop, --

Signed and Sealed this  
Third Day of September, 2019

Andrei Iancu  
*Director of the United States Patent and Trademark Office*